(12) United States Patent
Frank

(10) Patent No.: US 7,047,976 B2
(45) Date of Patent: May 23, 2006

(54) MEDICAL DEVICE FOR OVERCOMING AIRWAY OBSTRUCTION

(76) Inventor: Simon Jacob Frank, 11400 SW. 94th Ave., Miami, FL (US) 33176

( * ) Notice: Subject to any disclaimer, the term of this patent is extended or adjusted under 35 U.S.C. 154(b) by 191 days.

(21) Appl. No.: 10/610,399

(22) Filed: Jun. 30, 2003

(65) Prior Publication Data

US 2004/0261800 A1 Dec. 30, 2004

(51) Int. Cl.
*A61F 13/00* (2006.01)

(52) U.S. Cl. ............... 128/846; 128/201.23; 128/845; 602/35

(58) Field of Classification Search ............ 601/41–44, 601/39, 24, 25; 128/845, 846, 876, 207.11, 128/DIG. 26, 207.17, 202.18, 206.67, 207.14; 602/32–39; 5/627, 114, 6
See application file for complete search history.

(56) References Cited

U.S. PATENT DOCUMENTS

| | | | | |
|---|---|---|---|---|
| 3,461,858 A | * | 8/1969 | Michelson | ............... 601/41 |
| 4,097,038 A | * | 6/1978 | Jansen | ............... 5/637 |
| 4,297,999 A | * | 11/1981 | Kitrell | ............... 128/205.16 |
| 4,571,757 A | * | 2/1986 | Zolecki | ............... 5/628 |
| 5,494,048 A | | 2/1996 | Carden | |
| 5,531,229 A | * | 7/1996 | Dean et al. | ............... 128/866 |
| 6,196,224 B1 | | 3/2001 | Alfery | |
| 6,200,285 B1 | | 3/2001 | Towliat | |
| 6,510,852 B1 | * | 1/2003 | Shiery et al. | ............... 128/845 |
| 6,637,057 B1 | * | 10/2003 | Phillips et al. | ............... 5/637 |

* cited by examiner

*Primary Examiner*—Henry Bennett
*Assistant Examiner*—Shumaya B. Ali
(74) *Attorney, Agent, or Firm*—Ruben Alcoba, Esq.; Laurence J. Edson, Esq.

(57) ABSTRACT

A medical device for overcoming upper airway obstruction when a patient is placed in supine position. A cradle receives the patient's head, and the patient's head rests on and is secured to the cradle. Specifically, the head rests upon a first portion. The weight of the head upon the first portion anchors the entire device. A second portion has an adjustable band that generates an upward pull on the patient's chin, thereby opening the patient's upper airway. The first and second portions are generally perpendicular to each other.

22 Claims, 5 Drawing Sheets

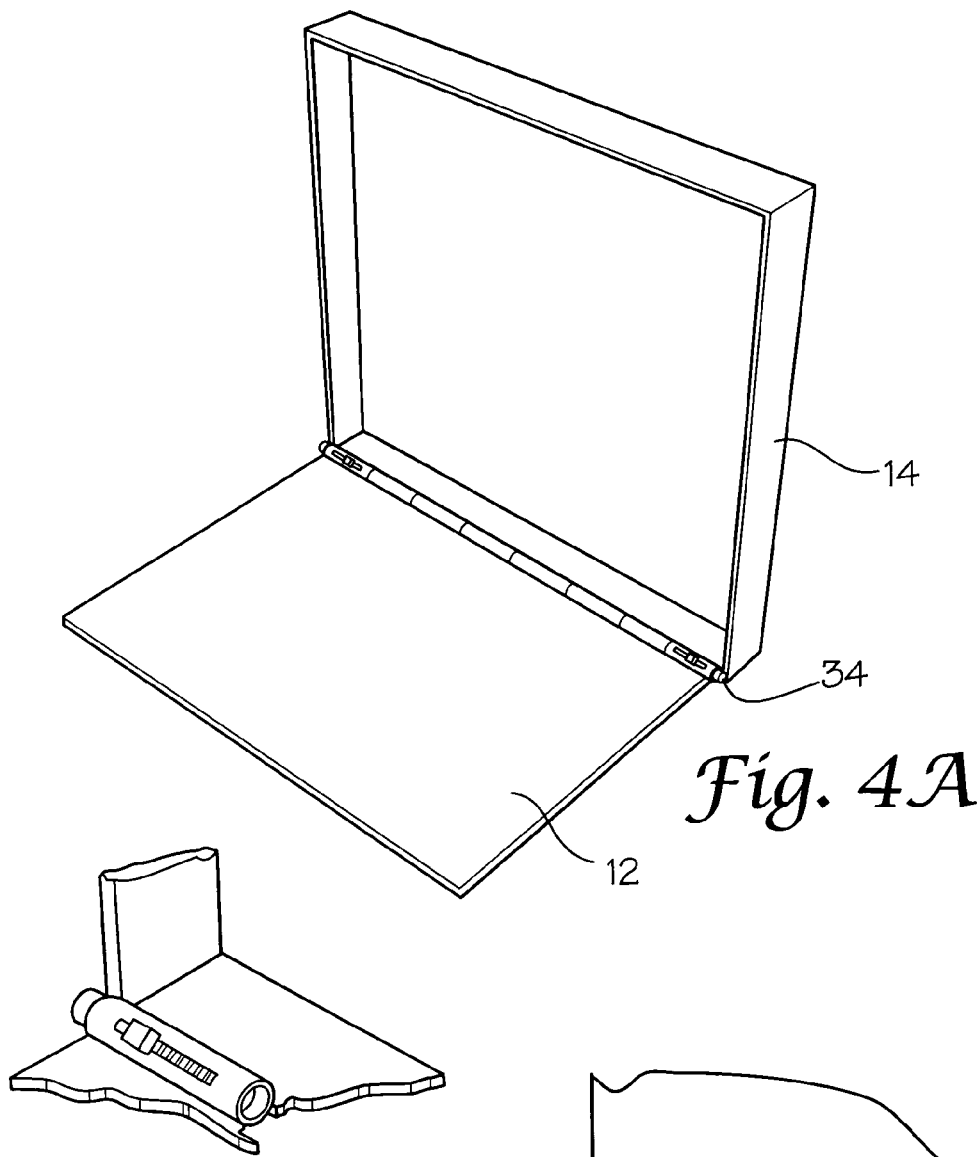
Fig. 4A
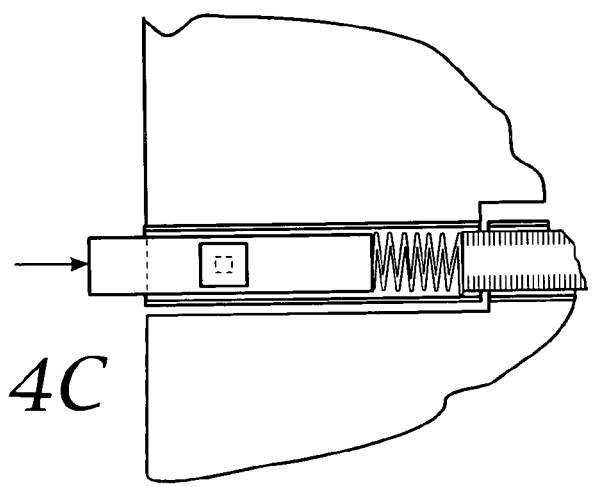
Fig. 4B
Fig. 4C

MEDICAL DEVICE FOR OVERCOMING AIRWAY OBSTRUCTION

BACKGROUND

Airway obstruction complications can arise when a patient is lying in the supine position while unconscious in an operating room or at any other emergency site. For example, when an unconscious person is resting in the supine position, the person either being sedated or anesthetized, gravity will pull the person's tongue downwards (towards the cervical spine) and the tongue will obstruct the airway and impede respiration, partially or completely. The above example might cause a life-threatening situation if the airway obstruction is not cleared, for hypoxemia and death can quickly ensue.

Anesthesiologists commonly overcome airway obstruction by tilting the patient's head backwards and pulling the chin up and away from the body (cephalad). Obstruction is avoided because the base of the tongue is attached to the mandible, and by pulling the chin up the tongue will be simultaneously pulled upward. This practice is very fatiguing and restricts the anesthesiologist's ability to perform other functions that require two hands.

An upper airway can also be maintained open by inserting various medical tubes into the body, for example, nasal-pharyngeal, oral-pharyngeal, end tracheal, laryngeal mask airway (LMA) and the cuffed oral pharyngeal. As of today, there are no medical devices in common use that attach externally to the face that will maintain an open upper airway.

In the past, practitioners have used surgical tape to attempt to maintain an open upper airway. Practitioners would secure tape around the chin of a patient and then attach the ends of the tape to an operating table. Tape procedures are unsatisfactory; for the tape attachment does not provide the upward pull required on the chin to maintain an open upper airway. Other complications with this procedure might be as follows: eye damage (this might occur when the tape securing the patient's chain graces the eye of the patient, gracing might occur if patient coughs or moves his head and skin trauma.

Chin props comprising a ball on the end of an arm secured to the operating room table have also been used to push the chin up. They too have proven unsatisfactory and are not commonly used. The reason that this type of chain prop is unsatisfactory is that they are large and cumbersome and get in the way of surgeons operating on the upper body. Furthermore, if misapplied they may constrict the airway. Chin props are designed to function with suitable operating tables that have complex mechanisms. Therefore, some chin props are not suitable for the use at accident sites or in ambulances transporting the injured.

Information relevant to attempts to address these problems can be found in U.S. Pat. Nos. 5,494,048, 6,200,285 B1, and 6,196,224 B1. However, each one of these references suffers from one or more of the following disadvantages:

1. Can cause eye damage;
2. Require suitable operating tables;
3. Obstruct the view of the patient;
4. Do not provide sufficient upward leverage to the chin;
5. Do not lend themselves to use in accident situations;
6. Do not prevent airway obstruction; and
7. Difficulties in removal of devices, should complications arise.

Inside and outside the operating room, a need exists for equipment that maintains an open airway. This equipment should be compatible and improve the effectiveness of oral-pharyngeal and nasal-pharyngeal airways and face masks. In the operating room, such equipment might reduce the need for the use of expensive endotracheal tubes in general anesthesia and allow mask anesthesia to be used for sedated patients. Outside the operating room, a need exists for compact equipment that will maintain an open airway and that can be used in cramped quarters such as an ambulance, hyperbaric chamber and an MRI chamber.

For the foregoing reasons, there is a need for a medical device that will maintain an open airway in the anesthetized and sedated patient lying in a supine position in an operating room and any unconscious patient lying in the supine position at any site. To be effective, the equipment should be safe and easy to use, and the procedure for its use should be simple and reliable. The equipment should free up the operators' hands; render oral and nasal pharyngeal airways more effective and not interfere with but facilitate the use of a mask. The equipment should be free standing and portable.

SUMMARY

The present invention is directed to a medical device that assists in overcoming airway obstruction when a patient, that may or may not be anesthetized, is unconscious and placed in the supine position. This device satisfies the following needs:

1. It frees the practitioner's hands to do other tasks while providing anesthesia to a patient;
2. It allows the practitioner to monitor the patient while the patient is anesthetized;
3. It is a compact and mobile device;
4. It does not cause eye damage to an anesthetized patient;
5. It provides the maximum flow of air to an anesthetized patient with out the use of the practitioner's hands;
6. Does not require the use of specific tables when operating the device; and
7. Allows for the easy removal of the device should an emergency situation arise.

The medical device for overcoming airway obstruction has an "L" shaped (in profile), rectangular cradle with first and second portions, wherein the first portion has a length at least a distance to allow a patient's head to rest on and act as an anchor to the cradle. The second portion has a length that is at least a distance to allow a band to be placed under a patient's chin and encircle the second portion. In this manner, an upward pull can be generated on the chin by the band when the second portion is placed in a perpendicular position to the first portion. The width of the cradle is at least a distance that allows for the clearance of a patient's side facial features when the patient's head rests on the first portion of the cradle and a band is made to encircle the chin of a patient and attach to the second portion of the cradle; and a band that attaches to the second portion of the cradle when the second portion is perpendicular to the first portion.

One of the many advantages of this invention is the simplicity of its construction. The two main elements of this invention are perpendicular portions and a band that easily attaches to one of the portions of the cradle after encircling the chin of a patient whose head rests on the other portion of the cradle after being placed in a supine position. The lack of numerous additional elements attests to the simplicity of construction and use of this device. Eye damage and irritation, injuries that have been previously caused by the prior art, are minimized by the presently claimed invention. This invention also aids those in the emergency transportation field, for they need to have the maximum use of their hands when dealing with unexpected emergency situations. For example, not having to worry whether the patient is getting sufficient airflow allows emergency personnel to care for other injuries sustained by the patient during the transport of the patient.

A further advantage to this invention is that it is a stand-alone medical device. The device does not need to be attached to any supporting devices to become operable. When a patient's head is made to rest on one of the sides of the perpendicular portions, the weight of the patient's head on the cradle is sufficient to secure the cradle on most surfaces so that an upward pull on the chin created between a band attached to the side of the cradle not carrying the weight of the patient's head and the patient's chin will be maintained during the use of this device. Remember, so long as this upward pull is maintained, the upper airway will be maintained open. Hence, it is key that the tension created with this device is not compromised and this is easily solved using the weight of the patients head as the anchor to the device.

Yet another advantage to this invention is that the placement of the band on the second portion insures that the band does not come in contact with the patient's eyes, this is very important for one cannot control when an unconscious person has an involuntary contraction or movement.

DRAWINGS

These and other features, aspects, and advantages of the present invention will become better understood with regard to the following description, appended claims, and drawings where:

FIG. 4 shows a perspective view of another version of the present invention, this embodiment has a means for pivoting the cradles and a locking means for maintaining the cradles in a perpendicular position.

DESCRIPTION

Figure 1:
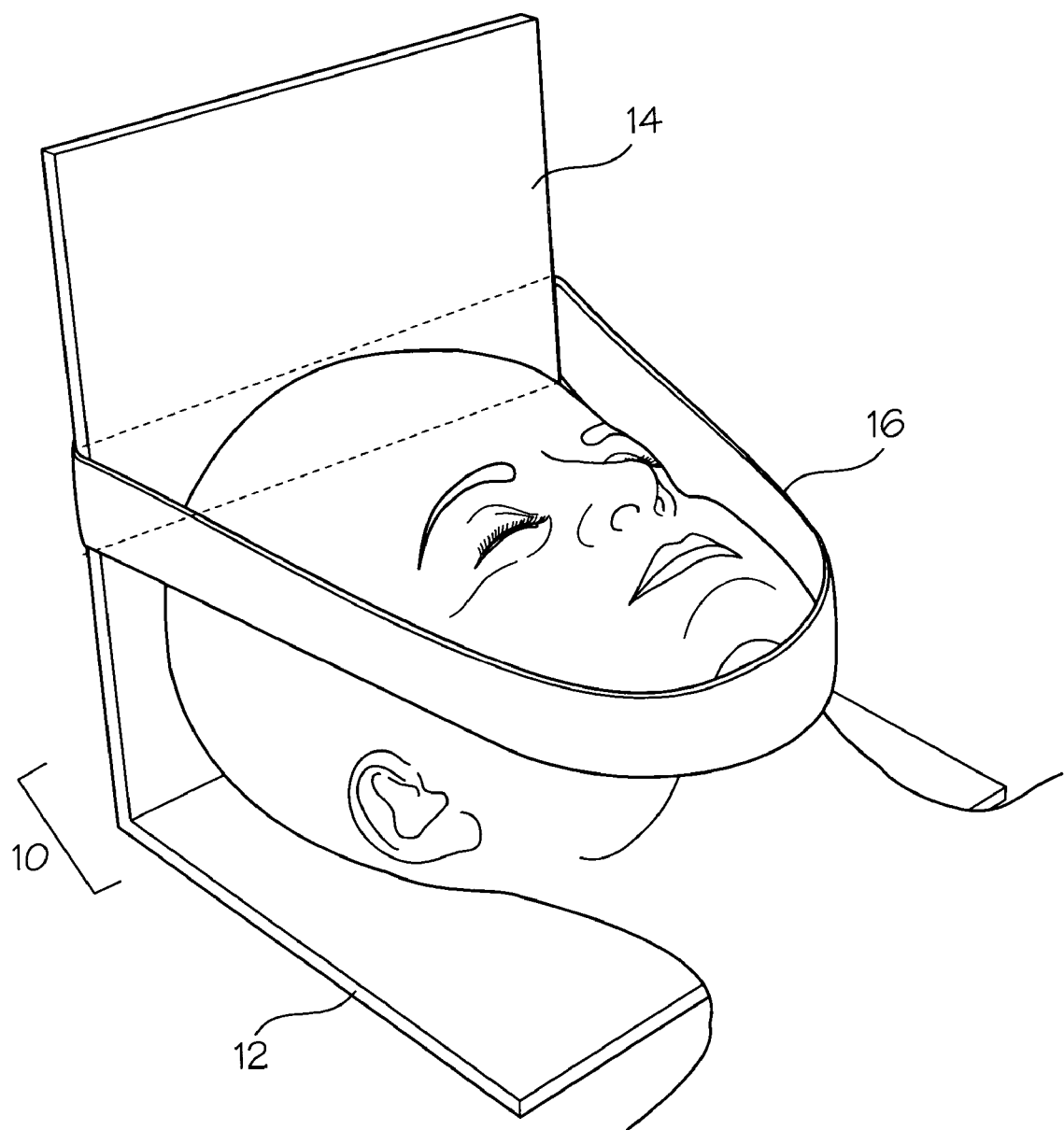
FIG. 1 shows a perspective view of the medical device with a patient in a supine position.

As shown in FIG. 1, a medical device used to overcome upper airway obstruction when a patient is in a supine position comprises a flat rectangular cradle 10 that has a first 12 and a second portion 14 wherein the first portion 12 has a length that is at least a distance that allows a patient's head to rest on and act as an anchor to the cradle and the second portion 14 is perpendicular to the first portion 12 and has a length that is at least a distance that allows a band 16 to be placed under a patient's chin and encircle the second portion 14 so that an upward pull can be generated on the chin by the band 16, and the cradle's width is at least a distance that allows for the clearance of a patient's side facial features when the patient's head rests on the first portion 12 of the cradle 10 and a band 16 is made to encircle the chin of a patient and attach to the second portion 14 of the cradle; and a band 16 that attaches to the second portion of the cradle when the second portion 14 is perpendicular to the first portion 12.

Figure 2:
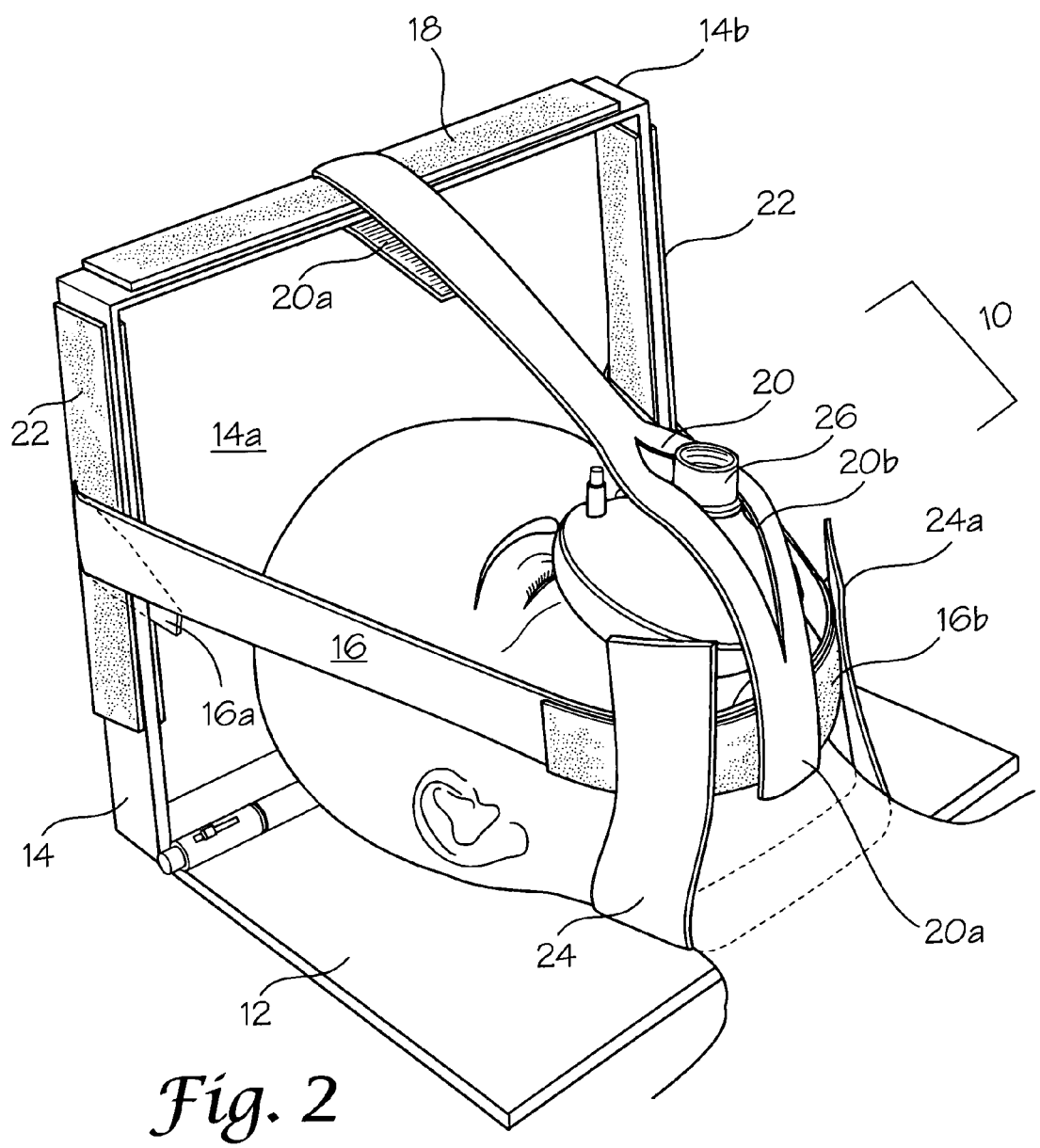
FIG. 2 shows a perspective view of another version of the medical device in use with a patient in a supine position.
Figure 3:
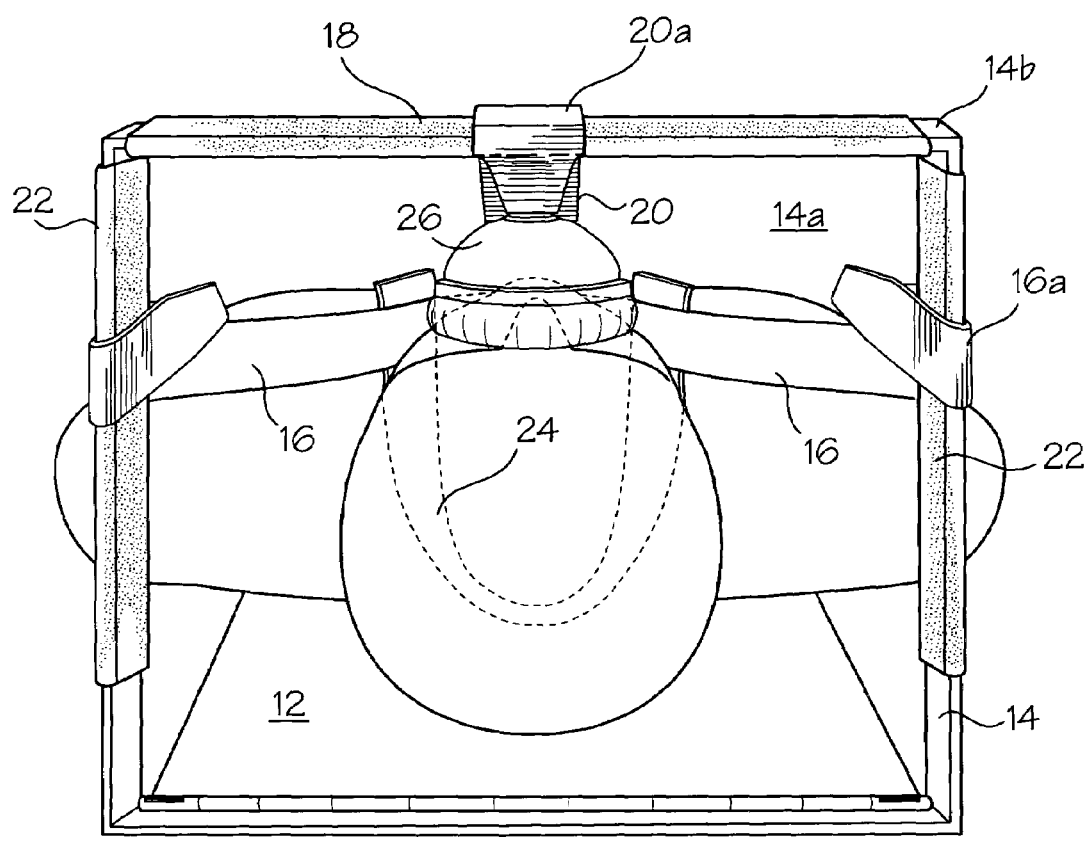
FIG. 3 shows a rear view of the medical device shown in FIG. 2, this view shows the second cradle having an aperture within the second cradle.
Figure 5:
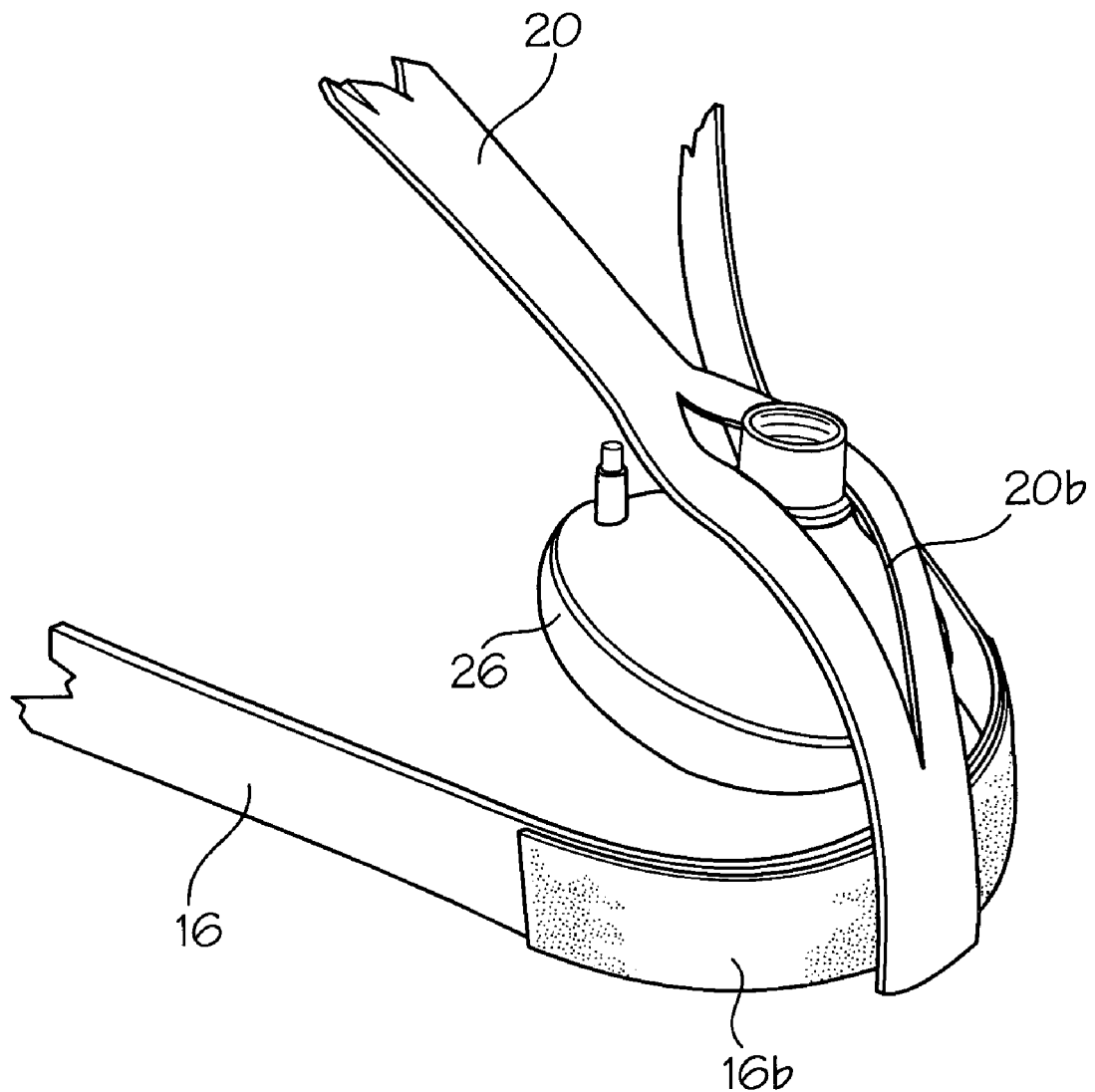
FIG. 5 shows a perspective of how the mask would attach to the first strap of the medical device and surround the nose and mouth of a patient in a supine position.

The cradle can be made of stainless steel, plastics or polymers. The length of first 12 and second 14 portions of the cradle must be at least a 1 to 1 ratio. The length of the first portion 12 should be at least of a length that will allow a patients head to rest on it and act as an anchor to the medical device. The length of the second portion 14 should be of at least of a length that will create an upward pull on the chin of a patient when a band 16 is made to encircle the chin of the patient, when a patient is placed in a supine position, and the second portion 14 of the cradle 10. In a preferred embodiment of the invention, the length of the cradles will be eight inches to twelve inches. Another embodiment of the invention has the first 12 and second 14 portions of the cradles being both eight inches in length. The width of the cradles is to be at least eight-inches, the preferred embodiment would have a width of twelve inches. The width has to be of sufficient length to allow for the clearance of the eyes when attaching the band 16 to the second portion 14 of the cradle 10. As seen in FIG. 2 and FIG. 3, the second portion 14 of the cradle can define an aperture 14a that will merely make the second portion of the cradles a physical skeleton to attach the band 16 or straps yet to be defined.

The band can be made of an elastic material that has a degree of tension sufficient to pull the weight of a person's chain upward (when the patient is placed in a supine position) when encircling the second portion of the cradle and the chin of the patient. As seen in FIG. 2, the band 16 can also be made of fabric and have two ends, if the band 16 is made of fabric, then it is preferable that the ends of the bands 16a have either hook or pile fasteners. When using a fabric band 16, it is essential that the second portion 14 of the cradle have two receiving means 22 located on opposite sides of the second portion 14 and running along the length of the second portion 14 and situated a sufficient height to allow for an upward pull to be generated on the chin of a patient when the band 16 is placed around the chin of the patient and the ends of the band 16a are attached to receiving means 22 of the second portion 14 of the cradle. The receiving means 22 will also comprise of either hook or pile fasteners, depending on what type fasteners the ends of the band 16a utilize.

As seen in FIG. 2, the medical device can further comprise of having a middle attachment means 18 attached second portion 14 of the cradle (middle attachment means 18 can simply be glued on to the second portion 14), the middle attachment means 18 will attach to the second portion 14 at the outer extremity of the second portion 14b and be centered and run parallel along the width of the cradle 10. The attachment means 18 can be made of a fabric and contain hook or pile fasteners. The middle attachment means 18 is attached to a first strap 20, the first strap 20 has either hook or pile fasteners at its ends 20a (whether hook or pile fastener will depend on what type of attachment means the ends are connecting too). The first strap 20 will connect to the second (middle juncture) of the band 16b surrounding the chin of the patient using means known in the art (either hook or pile fasteners, this all depends on what type of fasteners the band has at the middle juncture of the band 16b to accommodate the connection). The first strap might define a first strap slit 20b running parallel along the length of the first strap. The first strap serves a duel purpose, the first purpose is to further apply upward pressure to the chain and the second purpose is to allow for the placement of a mask 26 within the slit that would cover the mouth and nose of the patient. The mask 26 would be used to provide either oxygen and/or an anesthetic to the patient.

The medical device can further comprise a second strap 24, the second strap 24 having attachment means located at the ends of the strap 24a (the attachment means would be either hook or pile fasteners). The second strap would encircle the rear of the patient's neck and would attach to the middle juncture of the band 16b fasteners. The only purpose for the second strap 24 is to secure the band 16 to the patient's chin, the invention does not require the second strap 24; it is used only as a safety precaution.

As seen in FIG. 4, another embodiment of the invention would comprise of a pivoting means 34 for folding the medical device. The pivoting means 34 would facilitate the transport of the device and would most likely be used in the field by emergency personnel, such as paramedics. The pivoting means 34 would connect the first 12 and second 14 portions of the cradles and have a closed locking position and an opening perpendicular locking position 36. The locking means would be incorporated into the pivot by means known in the art. As a safety precaution, the pivoting means, when placed in the perpendicular position would be placed so that they would not be able to rotate further than the perpendicular. This could simply be accomplished by inserting a screw along side the pivot (s) in either of the portions (allowing the head of the screw to be raised at least a few centimeters above the pivot) so that the portion not containing the screw could not be pivoted beyond the perpendicular. All of the previous elements discussed could be incorporated into this embodiment of the invention.

A method of overcoming upper airway obstruction when a patient is in a supine position comprises the steps of placing the above mentioned medical device on a flat surface, resting the back of a patient's head on the first portion 12 of the cradle, and encircling the chin of the patient with the band 16 and attaching the rest of the band to the second portion 14 of the cradle, the band's attachment to the second portion 14 would be in a position sufficiently high so that an upper pull can be generated on the chin of the patient.

The above method describes the most rudimentary use of the medical device described in this application. The medical device's main purpose is to prevent the blockage of the upper airway. As stated before, this is accomplished by pulling the chin up and away from the body. The band 16 pulls the chin upward and the second portion 14 of the cradle is used to ensure that the pressure applied to the chain is maintained while freeing the hands of the practitioner. The medical device can also be used as means to secure a mask 26 to the face of a patient.

An advantage of the present invention is that a patient's eyes are never in danger of being damaged, for when the band is placed to encircle the chin of the patient and then attached to the second portion of the cradle, the band attaches to the second portion of the cradle at a position that does not allow the band to rub against the eyes.

Another advantage of the present invention is that when using the embodiment that defines an aperture in the second portion of the cradle, a patient can be monitored from behind the patient, there is no obstruction when monitoring the breathing of the patient.

A further advantage of the present invention is that it is compact and rudimentary in its nature. The device can be made operational by simply placing the device on a flat surface, placing a patient's head on the device (the patient being in a supine position) and encircling an elastic band around the patient's chin and the second portion of the cradle.

Yet further a further advantage to the device is that it does not require other structures to become operational, it is the ideal device for practitioners working in the field, paramedics.

Another advantage of the invention is the simplicity in which it can be taken off a patient should an emergency situation arise, you simply would pull the bands off the hook and pile fasteners.

A last advantage to this device is that it frees the hands of the operator, thereby allowing the operator to help the patient with other complications that the patient might be experiencing.

Although the present invention has been described in considerable detail with reference to certain preferred versions thereof, other versions are possible. Therefore the spirit and the scope of the claims should not be limited to the description of the preferred versions contained herein.

What is claimed is:

1. A medical device used to overcome upper airway obstruction when a patient is placed in a supine position comprising:
    a cradle having first and second portions; and a band attached to the second portion, wherein the first portion has a length that allows a patient's head to rest on and the second portion is perpendicular to the first portion and has a length at least a distance that allows a band to be placed under a patient's chin and encircle the second portion so that an upward pull can be generated on the chin by the band, the second portion's width is at least a distance that allows clearance of a patient's side facial features when the patient's head rests on the first portion and the band encircles the chin of a patient and attach to the second portion and the second portion has a middle attachment means located at the outer extremity of the second portion and the middle attachment means is centered and runs parallel to the width of the second portion; and wherein the ratio of the length of the portions is at least 1 to 1.

2. The medical device of claim 1, further comprising a first strap that attaches to the middle section of the band attached to the patient's chin, the middle section being the part of the band contacting the patient's chin, and the first strap further attaches to the middle attachment means.

3. The medical device of claim 2, wherein the band has two ends, each end having an attachment means for attachment to the second portion and wherein the second portion has two receiving means for attachment to the ends of the band, the receiving means of attachment being located on opposite sides of the second portion and situated to allow an upward pull on the patient's chin.

4. The medical device of claim 3, further comprising a second strap having two ends, each end of the second strap having attachment means that would attach to the band after the second strap encircles the back of the neck of the patient.

5. The medical device of claim 4, wherein the first strap defines a middle slit being centered and running along the length of the first strap.

6. The medical device of claim 5, further comprising a mask that is placed within the middle slit.

7. The medical device of claim 2, wherein the second portion defines an aperture sufficient in size to allow monitoring of the patient when the user of the device is standing behind the second portion of the plate.

8. The medical device of claim 7, wherein the second portion has a middle attachment means located at the outer extremity of the second portion and the middle attachment means is centered and runs parallel to the width of the second portion.

9. The medical device of claim 8, wherein the band has two ends, each end having an attachment means for attachment to the second portion and wherein the second portion has two receiving means for attachment to the ends of the band, the receiving means of attachment located on opposite sides of the second portion and situated to allow an upward pull on the patient's chin.

10. The medical device of claim 9, further comprising a second strap having two ends, each end of the second strap having attachment means that would attach to the band after the second strap encircles the back of the neck of the patient.

11. The medical device of claim 10, wherein the first strap defines a middle slit being centered and running along the length of the first strap.

12. The medical device of claim 11, further comprising a mask that is placed within the middle slit.

13. The medical device of claim 1, wherein the length of the cradle measures 20 inches and the portions are in a 2 to 3 ratio, and the width of the portions measures 8 inches.

14. A medical device used to overcome upper airway obstruction when a patient is placed in a supine position comprising: a first portion having a length of at least 8 inches and a width of 8 inches; a second portion having a length of 8 inches and a width of 8 inches, wherein the second portion define-s-an aperture sufficient in size to allow monitoring of the patient; a means for pivoting that attaches to the first and second portions alongside the width of the portions and allows the portion to fold on top of each other when pivoted in a first direction and when pivoted in a second direction the plates would rest perpendicular to each other; and a band that encircles and attaches to the second portion when the second portion is perpendicular to the first portion and the width of the second portion allows clearance of a patient's side facial features when the patient's head rests on the first portion.

15. The medical device of claim 14, further comprising a locking means for locking the portions in a perpendicular position.

16. The medical device of claim 15, wherein the second portion has a middle attachment means located at the outer extremity of the second portion and the middle attachment means is centered and runs parallel to the width of the second portion.

17. The medical device of claim 16, further comprising a first strap that attaches to the middle section of the band attached to the patient's chin, the middle section being the part of the band contacting the patient's chin, and the first strap further attaches to the middle attachment means.

18. The medical device of claim 17, wherein the band has two ends, each end having an attachment means for attachment to the second portion and wherein the second portion has two receiving means for attachment to the ends of the band, the receiving means of attachment being located on opposite sides of the second portion and being situated at a sufficient height to allow an upward pull on the patient's chin.

19. The medical device of claim 18, further comprising a second strap having two ends, each end of the second strap having attachment means that would attach to the band after the second strap encircles the back of the neck of the patient.

20. The medical device of claim 19, wherein the first strap defines a middle slit being centered and running along the length of the first strap.

21. The medical device of claim 20, further comprising a mask that is placed within the middle slit.

22. A method of overcoming upper airway obstruction when a patient is placed in a supine position comprising:
   placing the medical device of claim 1 on a flat surface;
   resting the back of the head of the patient on the first portion so that the head of the patient anchors the cradle; and
   encircling the band at a certain height of the second portion and around the chin of the patient so that an upward pull is created on the chin when the band contacts the second portion.

* * * * *